Figure 1:
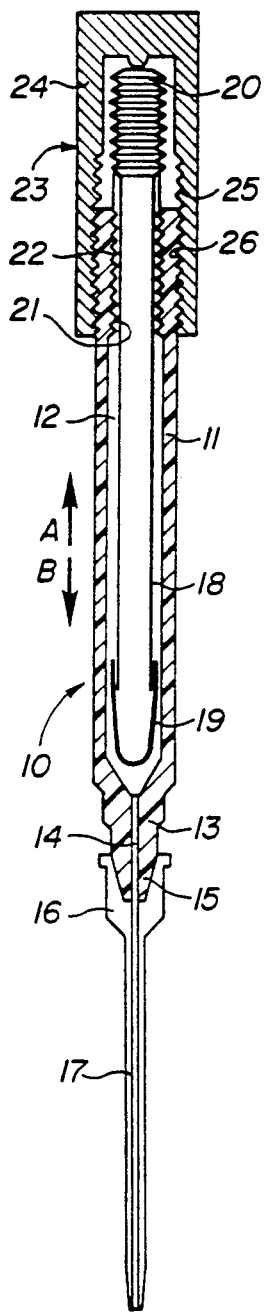

United States Patent

Gafner

[11] Patent Number: 5,308,343
[45] Date of Patent: May 3, 1994

[54] APPLICATION DEVICE FOR DEPOSITING A LIQUID SUBSTANCE LOCALLY ON A SURFACE TO BE TREATED

[76] Inventor: Paul-Félix Gafner, Là-Haut, Essert-Pittet 1435, Switzerland

[21] Appl. No.: 459,790
[22] PCT Filed: Jun. 22, 1989
[86] PCT No.: PCT/CH89/00120
  § 371 Date: Aug. 8, 1990
  § 102(e) Date: Aug. 8, 1990
[87] PCT Pub. No.: WO89/12480
  PCT Pub. Date: Dec. 28, 1989

[30] Foreign Application Priority Data
  Jun. 23, 1988 [FR] France ............... 88 08628

[51] Int. Cl.⁵ ............... A61M 35/00; A61M 5/178; A61M 5/00
[52] U.S. Cl. ............... 604/289; 604/295; 604/186; 604/211
[58] Field of Search ............... 604/289-301, 604/186, 211, 224

[56] References Cited

U.S. PATENT DOCUMENTS

| 2,534,310 | 12/1950 | Silverman | 604/295 X |
| 2,625,159 | 1/1953 | Roehrich | 604/289 X |
| 2,698,015 | 12/1954 | Brown | 604/295 X |
| 2,707,469 | 5/1955 | Feinstein | 604/295 |
| 2,784,882 | 3/1957 | DuBois | 604/289 X |
| 2,843,426 | 7/1958 | Nojima | |
| 2,990,563 | 7/1961 | Davidson | 604/289 X |
| 3,244,173 | 4/1966 | Berg | 604/300 X |
| 3,799,406 | 3/1974 | St. John et al. | 604/211 X |
| 3,815,785 | 6/1974 | Gilmont | 604/211 X |
| 3,820,698 | 6/1974 | Franz | 604/289 X |
| 4,045,096 | 8/1977 | Lidov | |
| 4,852,768 | 8/1989 | Bartsch | 604/211 X |
| 4,959,056 | 9/1990 | Dombrowski et al. | 604/211 X |
| 5,104,380 | 4/1992 | Holman et al. | 604/211 X |

FOREIGN PATENT DOCUMENTS

| 129867 | 8/1919 | United Kingdom . |
| 1148021 | 4/1969 | United Kingdom . |

Primary Examiner—Randall L. Green
Assistant Examiner—Elizabeth M. Burke
Attorney, Agent, or Firm—Davis, Bujold & Streck

[57] ABSTRACT

This invention concerns a device for applying a medicated solution on the skin for dermatological treatment. This applicator (10) essentially comprises an elongated tubular component (11) with an internal cavity (12) in which is fitted a piston (18) secured to the end of a piston rod (21) integral with a micrometer screw mechanism (23). A chamber (27) made in the inner cavity (12) between the piston (18) and plug (13) is designed to contain the therapeutic solution which may be taken in or discharged through capillary conduits (14 and 17) of the plug (13) and an applicator end (16). This applicator makes it possible precisely to meter and deposit a predetermined volume of the treatment solution on the exact place to be treated.

20 Claims, 2 Drawing Sheets

APPLICATION DEVICE FOR DEPOSITING A LIQUID SUBSTANCE LOCALLY ON A SURFACE TO BE TREATED

The present invention concerns an application device for the local deposition of a liquid substance onto a surface to be treated, particularly a medicinal solution onto a cutaneous surface for a dermatological treatment, this device having an elongated tubular element comprising an internal cavity, a micrometric-screw dosing mechanism, and a distribution tip provided with a capillary conduit communicating with the interior surface, the micrometric-screw dosing mechanism being designed to allow the volume of the internal cavity to be altered.

The dermalotogical treatment known as topical, by means of medicinal substances deposited onto the surface of a diseased skin, is normally carried out by means of brushes or applicators made of glass or of a synthetic material. The end of these applicators is often rounded in the form of a spatula with the aim of depositing the treatment solution onto the diseased skin. Sometimes these devices are replaced by glass tubes of small diameter comprising a capillary conduit, forming a sort of pipette.

These known devices have shown themselves to be inefficient or inadequate for the treatment of warts, actinic or seborrheic keratoses, acuminate condyloma or of certain skin cancers. In effect, with these devices the physician is practically incapable of precisely dosing the therapeutic substances to be used, and to apply them to the skin. Following on from this, these means of application are shown to be impractical and in particular, imprecise in use.

Applicators based on the principle of microcapillarity have specific drawbacks due to the fact that they develop an oil film at the interior of the capillary tube, which has to be rinsed with alcohol before use. This means that the pipette type of applicator is complicated, impractical and requires a relatively important preparation time before any application operation can actually be carried out.

The present invention proposes to obviate these various drawbacks by proposing an application device such as mentioned above, which is easy to use, of simple conception and structure and which allows a precise dosing of the therapeutic solution, together with a great precision in application of this solution onto the cutaneous surface to be treated.

Towards this end, the application device according to the invention is characterised in that the internal cavity contains at least one supple pocket containing a determined volume of gas, and in that the micrometric-screw dosing mechanism comprises a mobile element designed to compress to a greater or lesser extent, the said supple pocket so as to allow the volume of the said internal cavity to be altered.

According to a preferred embodiment, the supple pocket is open at one of its ends and communicates with the said capillary conduit by means of this end.

According to another embodiment, the supple pocket is closed.

In both cases, the supple pocket may be either a teat with smooth walls, or a teat with accordion-pleated walls.

According to another embodiment, the device comprises a first supple pocket lodged in the internal cavity of the elongated tubular element and a second pocket lodged in the distribution tip.

According to a particularly useful embodiment, the distribution tip is prefilled and contains the liquid substance to be deposited locally on the surface to be treated.

According to an interesting embodiment, the liquid substance to be deposited locally on a surface to be treated is contained in the said supple pocket.

For the case where the tubular element comprises two supple pockets, these may be lodged in the internal cavity of this tubular element.

According to a preferred form of construction, the micrometric mechanism may comprise a hood provided with a micrometric thread, threaded with a micrometric thread linked with the tubular element and designed to exert a force against the said supple pocket and to communicate variations of the volume to the air contained in the capillary conduit of the distribution tip.

In this case, it may comprise a tube lodged in the internal cavity of the elongated element, blocked at one of its extremities by a pocket designed to be compressed by the micrometric-screw mechanism and at its opposite end by a second supple pocket.

This tube is preferably fixed inside the internal cavity of the elongated tube by screwing.

According to one variant, the tubular element comprises an axial capillary conduit and two supple pockets respectively linked to the edges of this conduit.

One of these pockets is preferably lodged in the interior of a rotating hood which is axially mobile with respect to the tubular element and the other in the interior of the distribution tip.

Figure 2:
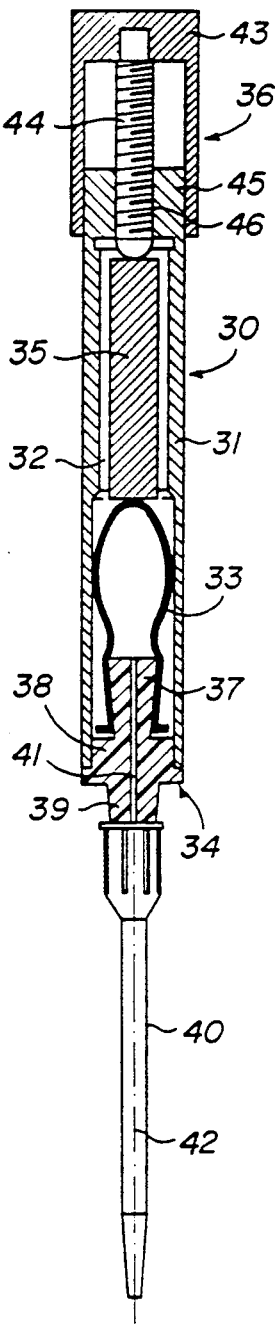
Figure 3:
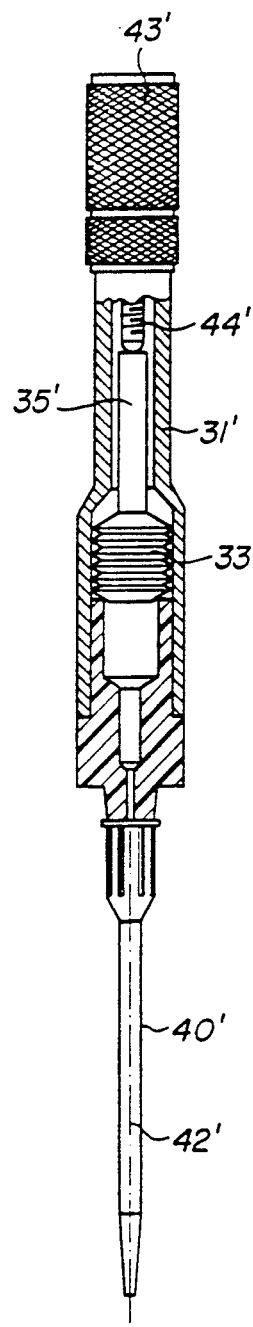
Figure 4:
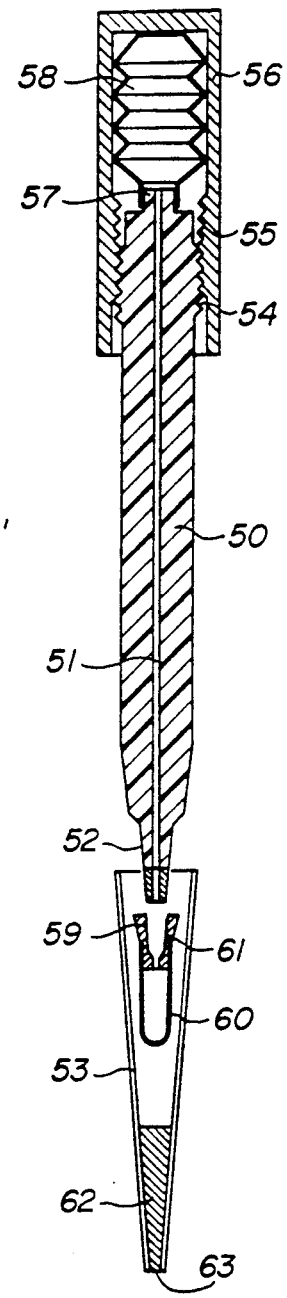
Figure 5:
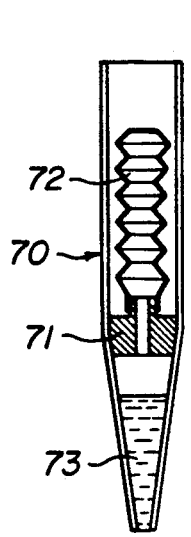

The present invention will be better understood by referring to the description of examples of the applicator device according to the invention and to the annexed drawing, in which:

FIG. 1 represents an axial cross-section of a particular embodiment of the applicator device according to the invention, FIG. 2 represents an axial cross-section of another form of an embodiment of the applicator device according to the invention, FIG. 3 represents a third form of an embodiment of the applicator device according to the invention, FIG. 4 represents a cross-section showing another embodiment of the device according to the invention, FIG. 5 represents a partial view of a tip adaptable to the application device represented in FIG. 4, and FIGS. 6–11 show different variations of distribution tips adapted to application devices such as those shown in FIG. 4.

With reference to FIG. 1, the application device 10 shown, is principally composed of an elongated tubular element 11, which may be thought of as the body of the device and which defines an internal cavity 12. At one of its ends, the tubular element 11 has a narrowed section 13 pierced axially by a capillary conduit 14. The said narrowed section has the form of a link cone 15 allowing a distribution tip 16 to be fitted, this tip also being pierced axially by an axial capillary conduit 17 which is connected with the capillary conduit 14 of the narrowed section 13.

The internal cavity 12 of the tubular element 11 of the application device 10 contains a tube 18 of a cylindrical form, the end nearest the distribution tip 16 being blocked off by a first supple pocket 19, and at its opposite end by a second supple pocket 20 having the form of a teat pleated like an accordion, which may be compressed then take up its initial position again. To this end, the tube 18 is mounted, for example by screwing, by means of a peripheral thread 21 in the tubular element 11 which is accordingly supplied with an internal thread 22.

In addition, the device comprises a micrometric-screw mechanism 23. This mechanism in fact comprises a hood 24 provided with an interior thread 25 which screws onto an external thread 26 of the cylindrical tubular element 11. The two threads 25 and 26 cooperate with each other and have a very small step, so that a rotation of a relatively high number of turns of the hood 24 causes a relatively small axial displacement of this hood. This displacement produces a force and compresses, to a greater or lesser extent, the teat 20.

The hood is designed to act in both directions, on the one hand "upwards", i.e. in the direction shown by the arrow A, which causes the drawing in of a certain quantity of therapeutic solution across the capillary conduit 17, and on the other hand "downwards", in the direction shown by the arrow B which has the effect of expelling a precise quantity of this solution across the capillary 17, and its deposition on the surface to be treated.

This device is held easily by one hand, and the hood 24 can easily be turned in either direction by the fingers of this same operator's hand. From this it follows that the operator has his other hand free, which is particularly important for ensuring a precise localisation of the medicinal solution on a determined place of a cutaneous surface. By means of the micrometric-screw dosing mechanism, the quantity of liquid expelled from the capillary conduit may be precisely controlled. It is noted that the liquid is only evacuated when the operator turns the hood and that this expulsion stops immediately when the operator stops turning the hood. Because of this he ca control by sight, in an extremely precise manner, the quantity of liquid to be deposited on the surface to be treated. Even though one of the essential applications of this device is in the medical therapeutic field, other applications may be envisaged. In particular, the deposition of special glues for glueing mechanical pieces or electronic components. This form of construction is particularly useful in that it allows the complete separation of the internal cavity of the tubular element from the tip which may contain aggressive substances intended for the envisaged treatment. The variation of the interior volume corresponds to a taking in, or an expulsion of the treatment liquid in the capillary conduit.

FIG. 2 shows another interesting form of the application device. The principle of this device, its proposed aims and the obtained results are substantially the same as those described above with reference to FIG. 1. The cutaneous application device 30 also comprises an elongated tubular element 31 which defines an internal cavity 32 in which are lodged on one hand a supple pocket 33 or teat, blocked at its open end by a stopper organ 34, and on the other hand by a pusher organ 35 capable of sliding in the interior of the cavity 32 under the action of a micrometric-screw mechanism 36 mounted at the extremity of the tubular element 31.

The stopper organ 34 comprises on the one hand a protuberance of a decreased diameter 37 which engages in the opening of the supple teat 33, and on the other hand a cylindrical section 38 of enlarged diameter which blocks the tubular element 31. This last section is equipped with a linking cone 39 to link it to the distribution cone 40. The stopper organ 34 is pierced by a capillary conduit 41 which joins an axial capillary conduit 42 piercing the distribution tip 40.

The micrometric screw dosing mechanism 36 comprises, as before, a milled hood 43 which is solid with a threaded rod 44 engaged in a threaded bore arranged in the end upper section 45 of the tubular element 31. In this form of embodiment, the threaded rod 44 comprises a free end 46 which can exert a pressure against the sliding pushing organ 35 intended to exert a compression on the supple teat 33. Such a compression has the aim of reducing the interior volume and expelling a determined quantity of treatment liquid across the capillary 42. The opposite movement is also possible by this system. In effect the supple walls of the teat 33 form a sort of return spring allowing the pusher organ 35 to be repushed when the threaded rod 44 is wound back up under the effect of an inverse rotation of the milled hood 43.

As before, the application device is capable of functioning by drawing in or by expelling according to the direction of rotation given to the milled hood 43. In addition the application device may be devised so as to form an organ comprising two complementary modules, of which one comprises the tubular element and the micrometric-screw dosing mechanism, and of which the other comprises the teat with supple wall 33, a stopper organ 34 adaptable to the open end of the tubular element 31 and a distribution tip 40. It is possible to deliver tips or complete modules comprising tips and/or teats prefilled with various solutions and to mount them, according to need, on the elongated element 31. Such a system avoids any handling of medical substances and avoids the obligation to proceed with a cleaning of the teat after using the applicator and before a new using of this applicator with a different therapeutic solution. In addition, this type of design protects the interior of the applicator against any damage from the vapours given off by the treatment liquid.

FIG. 3 shows another application device which constitutes a variant of the device shown by FIG. 2. Apart from the particular shape of the tubular element 31', the only difference is the replacement of the supple walled teat 33 by a closed compressible pocket 33' whose walls are pleated like an accordion, which facilitates its compression and its return to its initial position.

The same advantages as those described with reference to FIG. 2 apply to the device illustrated by FIG. 3. The materials used to make the pocket 33' may be different from those which are used for the manufacture of the teat 33. For this latter, the walls are made from a synthetic rubber or from an elastomeric plastic material. The pocket 33' may be made from a plastic material which does not belong to the class of elastomeric materials, given that the elasticity of this pocket is obtained by the accordion-like pleating of it.

A pushing organ 35', of cylindrical shape, slides in the interior of the cavity of the tubular element in function with the axial displacement of the threaded rod 44', itself linked to the milled hood 43'. This pushing organ could also be made solid with the threaded rod.

In this embodiment, the pocket 33 is compressed by the effect of the displacement of the pushing organ 35'. Contrary to what occurs in the device of FIG. 2 where a pressure exerted on the teat causes a backward flow of the liquid, a pressure on the pocket 33 has the effect of increasing the interior volume in the cavity of the elongated element 31′ and in consequence, causing liquid to be taken up in the capillary 42′ of the tip 40′.

The device shown in FIG. 4 is a variant of the device shown in FIG. 1. As in this example, it comprises an elongated tubular element 50 crossed from one end to the other by a conduit 51 which is preferably a capillary conduit. Next to one of its ends, the tubular element 50 has a substantially cone-shaped narrowed section which is adapted to receive a distribution tip 53. The opposite end section is equipped with an exterior thread 54 which is designed to connect with the interior thread 55 of a milled hood 56. A cylindrical tip 57 of decreased section bears a supple pocket 58 whose walls are preferably pleated like an accordion.

In the interior of the distribution tip 53 is mounted an element composed of a blocking stopper 59 which carries a second supple pocket 60. The blocking stopper 59 is pierced by a capillary conduit 61 which communicates with the interior of the supple pocket 60. In the diagram, the blocking stopper is not shown in its final position. In effect, in this position, the stopper is pushed hermetically against the internal walls of the distribution tip 53. In addition, this distribution tip is engaged on the extremity of the tubular element 50 so that the link between these two elements is hermetic. In the example shown, the distribution tip 53 is of the prefilled type and contains a treatment substance, for example a medicinal substance.

The space defined by the supple pocket 58, the capillary conduit 51, the capillary conduit 61 and the supple pocket 60 define a reference volume which may be varied by compressing the supple pocket 58 this caused by a rotation of the hood 56. The compression of the supple pocket 58 is felt at the level of the supple pocket 60, which has the effect of altering the volume of air situated over the level of the liquid substance 62. This increase in volume has the effect of pushing out a certain quantity of this substance, by an opening 63 positioned at the extremity of this tip. When the tip is, as shown in the figure, of the prefilled type, the user turns the hood 56 in one direction to expel the treatment substance from this tip. By contrast, when the tip is not of the prefilled type, i.e. when a quantity of substance must be previously taken up from an appropriate reservoir, the operator first of all compresses the supple pocket 58 then relaxes it to make the substance be taken up to a determined level in the distribution tip.

As mentioned before, this form of embodiment is particularly useful in that it protects the interior of the applicator device against the penetration of aggressive substances, or of the vapours of these substances. The tips may be designed to be disposable.

FIG. 5 shows another form of a tip adaptable to the device described above. This tip 70 comprises a blocking stopper 71 to which is attached a supple pocket 72 whose walls are pleated like an accordion. In this case, compression resulting from a decrease in volume in the supple pocket 58 causes a compression in the pocket 72 which is transmitted to the treatment liquid 73 contained in the end cone of the distribution tip 70.

Figure 6:
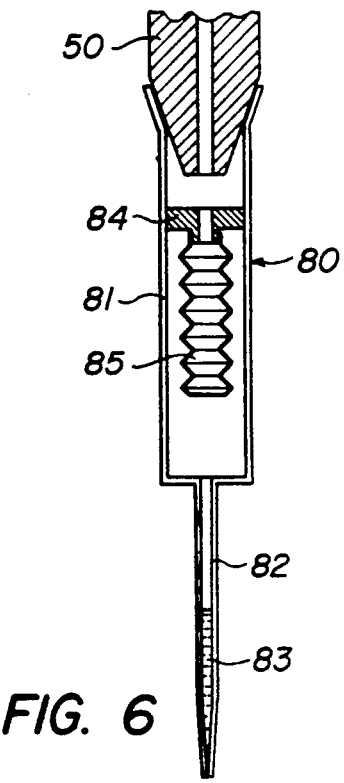

FIG. 6 shows another form of an embodiment of the tip shown in FIG. 5 adapted to a tubular element 50 such as that shown in FIG. 4. In this variant, the distribution tip 80 is composed of a substantially cylindrical upper element 81 and a lower capillary element 82 which contains a treatment substance 83. The upper element 81 is blocked by a blocking stopper 84 to which is added a supple pocket 85 whose walls are pleated like an accordion. As before, the variations in volume undergone by the upper pocket 58 are transmitted to the supple pocket 85 causing the displacement in one direction or another, of a treatment substance 83 contained in the capillary end 82 of the distribution tip.

Figure 7:
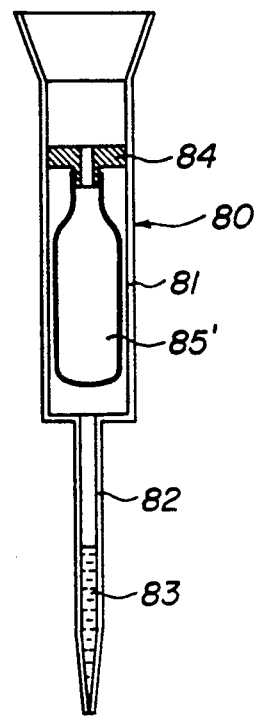

FIG. 7 shows a variant of the tip shown in FIG. 6. In fact, this variant differs in the shape of the pocket 85′ which has smooth walls.

Figure 8:
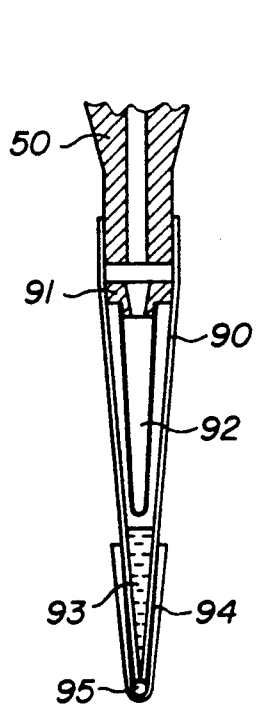

FIG. 8 shows a variation in which the distribution tip 90 contains a blocking stopper 91 to which is attached a supple pocket 92, with smooth walls, which take up the variations in volume caused by the compression of the superior supple pocket 58 mounted on the upper extremity (not shown) of the elongated tubular element 50. Also in this case, the distribution tip is of the prefilled type and contains a treatment substance 93. This tip is blocked by a hood 94 which may be engaged by pushing or by screwing on the end point of this tip. A ball 95 insures the blocking of the opening of this tip.

Figure 9:
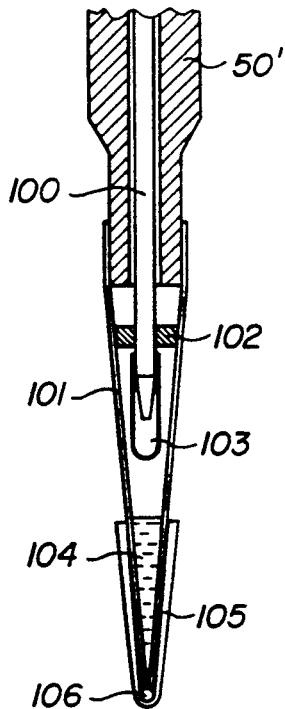

FIG. 9 shows another variant in which the elongated tubular element 50 of the application device contains a tubular element 100 which continues towards the interior of the distribution tip 101 across a stopper means 102 and which carries a supple pocket 103. This tip is also of the prefilled type and contains a treatment substance 104. It is blocked by a closing cone 105 containing a blocking ball 106.

Figure 10:
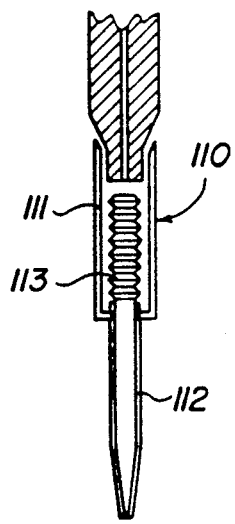

FIG. 10 shows another variant of a tip 110 comprising a superior cylindrical element 111 continued by a point 112. The upper part 111 contains a supple pocket 113 whose walls are pleated like an accordion. This pocket is attached to the point 112 so that any modification in the volume of this pocket causes liquid contained in the point to be taken up or expelled.

Figure 11:
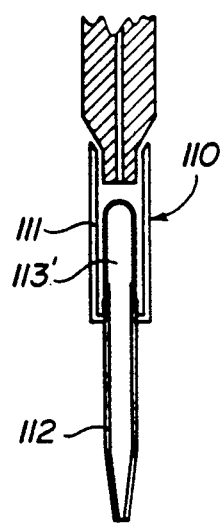

FIG. 11 is a similar view in which the pocket 113′ has smooth walls. The principle of functioning is the same in both cases.

The present invention is not limited to the forms of embodiments described but may undergo different modifications and be presented under different variants obvious for those skilled in the art. The shape and sizes of the different components may be adapted to the conditions of use of the applicator.

I claim:

1. An application device for local deposition of a liquid substance onto a surface to be treated, particularly a medicinal solution onto a cutaneous surface for a dermatological treatment, said device having an elongated element comprising an internal cavity having a volume, a micrometric-screw dosing mechanism located at a second end of the elongate element, and a distribution tip, located at a first end of the elongate element, provided with a capillary conduit communicating with said internal cavity, sand adjustment of the micrometric-screw dosing mechanism causing the volume of said internal cavity to be altered, wherein the internal cavity (12) contains at least one supple pocket containing a predetermined volume of a fluid, and the micrometric-screw dosing mechanism (23) comprises a mobile element for at least one of compressing and allowing expansion of said at least one supple pocket (20) so as to vary the volume of said at least one supple pocket and cause the volume of said internal cavity to be altered thereby controlling flow of the liquid substance into and out of said device.

2. A device according to claim 1, wherein said at least one supple pocket is a closed pocket and has bellowed walls which facilitate compression and expansion of said at least one supple pocket.

3. A device according to claim 1, wherein said at least one supple pocket seals the end of the capillary conduit which communicates with the internal cavity and the liquid substance to be deposited locally on a surface to be treated is contained in said at least one supple pocket and is dispensable, via the capillary conduit, through the distribution tip.

4. A device according to claim 1, wherein said micrometric-screw dosing mechanism (23) comprises a hood (24) provided with a micrometric female thread (25) threadedly engaged with a micrometric male thread (26) carried by the elongate element (10), and said hood is adjustable to exert a pressure on said at least one supple pocket (20), via a pusher member, and causes variation in the volume of the fluid in said at least one supple pocket.

5. An application device for local deposition of a liquid substance onto a surface to be treated, said device having a body comprising an elongated tubular element having first and second ends, a micrometric-screw dosing mechanism mounted on the second end of the elongated tubular element and a distribution tip mounted on the first end of the elongated tubular element, the elongated tubular element having an internal cavity defining an internal cavity volume comprising an inner space of the elongated tubular element and an inner space of the distribution tip and adjustment of the micrometric-screw dosing mechanism causing the volume of the internal cavity to be altered, wherein one supple pocket is connected to the tubular element and located within the internal cavity, the internal cavity contains a predetermined volume of a fluid, and the micrometric-screw dosing mechanism communicates with the one supple pocket so as to alter the volume of the one supple pocket and thereby vary the volume of the internal cavity.

6. A device according to claim 5, wherein said device comprises only the one supple pocket contained inside of the elongated tubular element and the one supple pocket is hermetically sealed with the elongate tubular element adjacent the first end of the tubular element and communicates with the distribution tip by means of a capillary conduit.

7. A device according to claim 6, wherein the supple pocket is a smooth-walled teat.

8. A device according to claim 6, wherein the supple pocket is a teat with bellowed walls.

9. A device according to claim 5, wherein said device comprises only the one supple pocket contained inside of the elongated tubular element, and the one supple pocket is a closed pocket and located inside of the internal cavity, and an intermediate pusher mechanism provides communication between the micrometric-screw dosing mechanism and the one supple pocket.

10. A device according to claim 9, wherein the supple pocket is a smooth-walled teat.

11. A device according to claim 9, wherein the supple pocket is a teat with bellowed walls.

12. A device according to claim 5, wherein the one supple pocket is connected to the tubular element via a first end of a tube having an elongate conduit extending therethrough, a second end of the tube is connected to a second supple pocket which is located adjacent and interacts with the micrometric-screw dosing mechanism and at least the one supple pockets is contained inside of the elongated tubular element.

13. A device according to claim 5, wherein the distribution top is prefilled and contains the liquid substance to be deposited locally on the surface to be treated.

14. A device according to claim 13, wherein the liquid substance to be deposited locally on a surface to be treated is contained in the supple pocket contained in the distribution tip.

15. An application device for local deposition of a liquid substance onto a surface to be treated, said device having a body comprising an elongated tubular element having first and second ends, a micrometric-screw dosing mechanism mounted on the second end of the elongated tubular element and a distribution tip mounted on the first end of the elongated tubular element, the elongated tubular element having an elongate conduit with first and second opposed ends, the first end communicating with a first supple pocket and the second end being sealed by a second supple pocket, an internal cavity having an internal cavity volume comprising at least an inner space of the distribution tip, and adjustment of the micrometric-screw dosing mechanism causing the volume of the internal cavity to be altered, wherein the first supple pocket defines a supple pocket volume, the internal cavity contains a predetermined volume of fluid, and the micrometric-screw dosing mechanism communicates with the first supple pocket, via the second supple pocket and the elongate conduit, so as to alter the volume of the first supple pocket so as to thereby cause the volume of the internal cavity to be varied.

16. A device according to claim 15, wherein the first supple pocket is located inside of the elongated tubular element and the second supple pocket is contained inside the distribution tip.

17. A device according to claim 15, wherein at least one of the two supple pockets is a teat with bellowed walls.

18. A device according to claim 15, wherein the tube has a capillary conduit.

19. A device according to claim 15, wherein the micrometric-screw dosing mechanism comprises a rotating hood provided with a micrometric female thread threadedly engaged with a micrometric male thread of the tubular element for exerting a pressure against the second supple pocket and thereby causing variation of the volume of fluid in the first supple pocket located in the internal cavity of the distribution tip.

20. A device according to claim 19, wherein the second supple pocket is situated under a rotating hood axially mobile with respect to the tubular element, and the first supple pocket is located within and at least partially defines the internal cavity of the distribution tip.

* * * * *